United States Patent [19]

Morey

[11] Patent Number: 4,607,529
[45] Date of Patent: Aug. 26, 1986

[54] VIBRATION ANALYSIS

[76] Inventor: John Morey, 3 Pigeon Bank Lane, Warrandyte, Victoria 3134, Australia

[21] Appl. No.: 712,445

[22] Filed: Mar. 18, 1985

[30] Foreign Application Priority Data

Mar. 21, 1984 [AU] Australia .............................. PG4171

[51] Int. Cl.$^4$ ............................................ G01N 29/00
[52] U.S. Cl. ..................................................... 73/660
[58] Field of Search .................. 73/660, 661, 593, 602

[56] References Cited

U.S. PATENT DOCUMENTS

4,426,641  1/1984  Kurihara et al. ..................... 73/660
4,429,578  2/1984  Darrel et al. ........................ 73/660

Primary Examiner—Anthony V. Ciarlante
Attorney, Agent, or Firm—Stevens, Davis, Miller & Mosher

[57] ABSTRACT

The present invention provides a method for measuring vibration in a machine including a member under periodic motion. To measure vibration in a rotating shaft (11) a first signal comprising a series of impulses, one impulse occurring each shaft revolution, is generated by a proximity probe (20) and a modulator/demodulator (22). The first signal is transmitted to channel A of a FFT spectrum analyzer (19) and a second signal, which varies in time with respect to displacement of the shaft (11), is produced by a proximity probe (14) and a modulator/demodulator (18) and fed to channel B of the FFT analyzer (19). The second signal is fourier transformed by analyzer (19) into the frequency domain to obtain reconstruction magnitude signals each indicative of the magnitude of one of the first twelve harmonics of the transformed second signal. The first signal is fourier transformed by the analyzer (19) synchronously with the second signal to obtain the phase angle differences between the respective harmonic components of each signal for the first twelve components. The mark to space ratio of the first signal is chosen to be less than one-twelfth so that the phase angles of the first twelve harmonic components of the fourier transformed first signal are known to be zero.

16 Claims, 5 Drawing Figures

VIBRATION ANALYSIS

BACKGROUND OF THE INVENTION

1. Field of the Invention

This invention relates to a method for dynamic analysis of vibration of machinery, and in particular, to a method for measuring vibration in a machine. Measurement of the vibration allows analysis of the causes of vibration and the analytical determination of modifications to minimise vibration.

In machinery having a rotating member, for example having a shaft mounted for axial rotation by means of bearings and driven in rotation within a casing, excessive vibration is undesirable and may lead to failure of the machine.

2. Description of the Prior Art

Hitherto, analysis of vibration of machinery has been conducted by measuring vibration displacement using special transducers to obtain a signal which varies in time with respect to displacement of a member. Usually a number of transducers are used to obtain displacement measurement in three mutually perpendicular directions. In the case of a machine having a rotating shaft disposed within a casing, the absolute displacement of the shaft is obtained by having transducers mounted to the machine casing to measure relative displacement of the shaft with respect to the casing and having a further series of transducers mounted to the casing to measure the displacement of the casing with respect to ground. The signals from the transducers measuring displacement in corresponding directions are then summed by means of a suitable analogue circuit to produce a vibration signal indicative of the absolute displacement of the shaft with respect to ground in each measured direction. In practice measurements are typically made on a horizontal and vertical axis each perpendicular to the shaft and in a direction parallel with the axis of the shaft. In this prior art arrangement is essential that the two transducers measuring displacement in the plane perpendicular to the shaft axis measure displacement in mutually perpendicular directions so that the obtained displacement signals can be displayed for example on a cathode ray oscilloscope as a function of time. Such a display produces a Lissajous figure which is the motion of the shaft axis and is termed the shaft orbit. The difficulty with this type of analogue information is that it is difficult to simultaneously display a meaningful representation of the displacement of the shaft in three directions simultaneously and it can only be done one bearing at a time for one harmonic at a time. The harmonics that can be analysed are also generally restricted to those having a frequency of one half, once, and twice shaft speed. In addition it is difficult and time consuming to perform any further harmonic analysis and calculations using the data since these must all be conducted by analogue means. In addition, the analogue signals can only be stored, for example, by recording on a tape recorder or some other suitable media.

Displacement measurement of rotating shafts in particular also requires correction for shaft imperfections or metal permeability changes that affect the transducer output. Accordingly, it is necessary to conduct a procedure known as a "slow roll" measurement which is the measurement of displacement at a slow shaft speed at which vibration effects can substantially be ignored and a calibration of the displacement measuring apparatus obtained relative to a known position on the shaft. This value is then subtracted from the absolute displacement data obtained as outlined above to give a true measure of absolute displacement. This subtraction requires a complex analogue filtering and off-setting process and can only be achieved for any one vibration harmonic at a time and further adjustment is required to perform the subtraction for each other harmonic of interest. The term harmonic as used herein is to be understood as including both integer and fractional harmonics. Since the subtraction is essentially by analogue means it is necessary to record the "slow roll" signal on a magnetic tape or other suitable device so that it can be reproduced for synchronous subtraction during vibration measurements at normal shaft rotating speeds. The storage of "slow roll" data is particularly important since some machines, such as turbine driven generators are stopped or slowed as infrequently as once every few years. "Slow-roll" data can only be obtained at these times and must be accurately stored for long periods. Hitherto, most storage has been by way of analogue tape recording which is clumsy to reproduce and not totally reliable.

Other disadvantages of the prior art analysing techniques include the restriction that because of the complexity of the analogue manipulation involved, vibration at each bearing in a machine for example, has to be measured and treated individually. This presents a serious limitation on the effectiveness with which a shaft can be analysed for balance quality in relation to harmonics of shaft speed frequency, alignment in relation to harmonics of shaft speed and twice shaft speed frequency, and looseness in relation to integer and fractional harmonics of three times shaft speed and greater frequency. The only effective balancing procedure is a process involving the placing of a number of trial weights at each balance plane and monitoring the difference of these weights at each bearing separately.

Because of the analogue nature of the vibration measurement data hitherto obtainable, it is not possible to accurately calculate various forces within the shaft so as to determine whether the vibration is caused for example by shaft imbalance, bearing misalignment, or other faults such as looseness and physical damage to the shaft.

SUMMARY OF THE INVENTION

The present invention has as an object to provide improved methods for measuring and analysing machine vibration.

The invention consists in a method for measuring vibration in a machine including a member under periodic motion, said method comprising the steps of:

(a) selecting specific vibration harmonic components to be measured;

(b) generating by first sensor means a first signal that repeats every period of said motion to provide a reference to a known position on the member, the transform into the frequency domain of said first signal having known harmonic component phase angles relative to said known position for all said selected harmonic components;

(c) generating by second sensor means a second signal which varies in the time domain with respect to a vibration characteristic of the machine;

(d) transforming the second signal into the frequency domain to derive a plurality of third (reconstruction magnitude) signals each indicative of the magnitude of one of the selected harmonic components of the transformed second signal, and synchronously transforming the first signal into the frequency domain to derive a fourth signal for each selected harmonic, each fourth signal being indicative of the phase angle difference between corresponding harmonic components of the transformed second signal and the transformed first signal; and (e) storing said third signals and said fourth signals.

For preference, the method further comprises the steps of obtaining for each selected harmonic component a fifth (reconstruction phase angle) signal indicative of the difference between each said fourth signal and a corresponding one of a plurality of sixth signals, each one of said sixth signals being indicative of one of the known harmonic component phase angles of said first signal; and storing said fifth signal.

Also for preference, the transform of the first signal and the second signal into the frequency domain comprises a fourier transform.

In one embodiment the member under periodic motion comprises a rotating shaft and wherein the reference signal repeats every shaft revolution. Preferably, the first signal comprises a series of impulses, one impulse occurring each shaft revolution which is generated by a suitable transducer located adjacent the rotating shaft which produces a signal change each time a reference point on the shaft rotates past the transducer. The mark to space ratio of the first signal is preferably less than 1/n, where n is the total number of selected harmonics so that the known harmonic component phase angles of the first signal for each selected component are zero.

The preferred embodiments of the invention permit the first and second signals four to be generated with the use of standard single purpose transducers. Only such transducers are necessary to measure vibration of any one member. The vibration information in the form of reconstruction magnitude values and reconstruction phase angle values allows analysis of operational mode shapes of relative displacement and absolute relative displacement by means of vector algebra. In addition, the stored signals can be used to selectively construct vibration wave forms of the member.

The present invention also permits "slow roll" data to be easily stored as a number of reconstruction magnitude values and corresponding reconstruction phase angle values. The "slow roll" data can therefore be readily and accurately reproduced.

Since the data is in easily manipulable form this can be represented in three dimensions by a suitable plotter or on a suitable video screen. The form of the data also allows any selected combination of harmonic components to be used in representation of a particular wave form. The enables the difference between for example, misalignment and imbalance to be detected since imbalance generally involves a high first harmonic vibration component whereas misalignment involves increased second and higher harmonic vibration components and 180° phase angle changes across flexible couplings.

The easily manipulable form of the waveform data also allows the forces at the bearings in a shaft, for example to be accurately calculated so that a suitable weight correction for misbalanced shafts can be determined without the need for a number of trial balances.

DESCRIPTION OF THE PREFERRED EMBODIMENT

Figure 1:
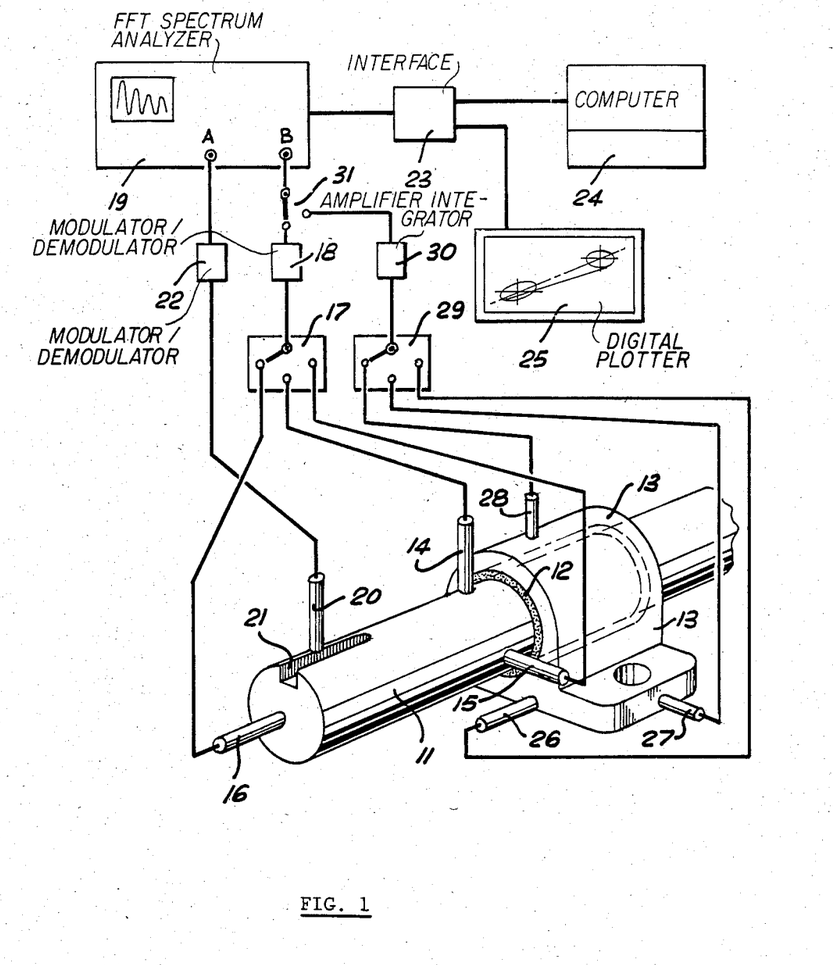
FIG. 1 is a schematic block diagram of the apparatus used in a preferred method for obtaining waveform reconstruction data for a vibrating member.

FIG. 1 illustrates the apparatus used in the obtaining of time domain waveform reconstruction data for a vibrating member in accordance with the method of the preferred embodiment. A rotating shaft 11 is shown passing through a bearing 12 located in a casing 13. Three proximity probes 14, 15 and 16 are located adjacent the shaft. Probes 14 and 15 are positioned perpendicular to the axis of shaft 11 and measure displacement respectively in substantially horizontal and vertical directions. The probe 16 is positioned parallel to the axis of the shaft 11 to measure axial displacement. Suitable proximity probes are sold under the trade mark Indicon. The probes 14, 15 and 16 are connected via a three way switch 17 and an Indicon modulator/demodulator 18 and a further two way switch 31 to the channel B input of a FFT spectrum analyser 19. A further Indicon proximity probe 20 is positioned adjacent the shaft 11 adjacent the rotational path of a keyway 21. The proximity probe 20 is connected via an Indicon modulator/demodulator 22 to channel A of the analyser 19. The analyser 19 is preferably a Hewlett Packard model 3582A. Three substantially conventional accelerometers 26, 27, 28 are used to measure the acceleration of the casing 13 in three substantially mutually perpendicular directions. The accelerometers are connected via a three way switch 29 to a charge amplifier and integrater 30. The amplifier and integrator 30 amplifies and twice integrates the signal from the accelerometer 26, 27 or 28 selected by operation of switch 29. The integrated signal is a displacement signal and can be fed by operation of switch 31 to channel B of analyser 19. The amplifier and integrater is preferably a Tensor Systems Mark IV charge amplifier.

The analyser 19 is connected via an interface 23 to a computer 24 and a digital plotter 25. The interface is preferably a Hewlett Packard HPIB interface and the computer is preferably a Hewlett Packard HP85B or Series 200 desk top computer. The digital plotter is a HP7470A also manufactured by Hewlett Packard.

According to the preferred method, time domain wave form reconstruction data for a vibrating member is obtained by generating a first signal that repeats every shaft revolution by means of proximity probe 20 and modulator/demodulator 22. The signal provides a reference to a known position on the shaft by comprising a series of impulses, one impulse occuring at each revolution of the shaft when the keyway 21 passes proximity probe 20. The mark to space ratio of the signal is less than 1/n where n is the number of selected vibration harmonics to be included in the analysis so that the fourier transform of the first signal has harmonic components phase angles equal to zero for all the selected harmonic components.

A sensor means comprising proximity probe 15 measures a second signal which varies in the time domain with respect to a vibration characteristic of the member. The vibration characteristic is displacement of the shaft 11 toward and away from the proximity probe 15. The second signal is fed via switches 17 and 31 to channel B of the analyser 19 simultaneously with the first signal being fed to channel A, and the analyser 19 fourier transforms the signals into the frequency domain by a fast fourier transform (FFT) technique.

The fourier transform of a time varying signal is written in terms of an infinite sum of cosine waves in the form $$A_1 \cos \alpha_1 + A_2 \cos 2\alpha_2 + \ldots + A_n \cos n\alpha_n + \ldots$$

where An is the magnitude of the nth vector component and $\alpha_n$ is the phase angle of the nth cosine wave summed.

Thus the fourier transform of the signal fed to channel A of the FFT analyser 19 can be written $$A_1 \cos \phi_{A1} + A_2 \cos \phi_{A2} + \ldots + A_n \cos \phi_{An} + \ldots$$

and similarly the fourier transform of the signal fed to channel B of the FFT analyser 19 can be written $$B_1 \cos \phi_{B1} + B_2 \cos \phi_{B2} + \ldots + B_n \cos \phi_{Bn} + \ldots$$

The terms $B_n$ are the reconstruction magnitude values indicative of the magnitude of the harmonic components of the fourier transformed second signal fed to channel B of the FFT analyser 19. The terms $\phi_{An}$ and $\phi_{Bn}$ are the phase angles of the harmonic (cosine wave) components of the fourier transformed signals. If the values of $B_n$, $\phi_{An}$ and $\phi_{Bn}$ are known for $n=1$ to a selected number of harmonics then the time varying displacement waveform measured by the proximity probe 15 can be represented as n vector components expressed relative to a known position on the rotating shaft, namely the keyway. The FFT analyser 19 provides a sufficiently accurate measurement of the reconstruction magnitude values $B_n$ of the harmonic components.

Although the FFT analyser 19 can directly provide a measure of the phase angles $\phi_{An}$ and $\phi_{Bn}$, the measured values are known to contain a significant error because of random and periodic variations in the operating speed and vibration of the machine containing the vibrating member, here shaft rotation speed. These variations necessitate signal averaging to obtain a representative measurement of magnitude and phase angle by the analyser 19. The signal averaging causes errors in the measured phase angles particularly in the phase angles corresponding to higher order harmonics. The errors are however, identical for components of the same harmonic frequency.

In accordance with the present method the FFT analyser 19 is used to directly determine the phase angle difference between corresponding harmonic components of the fourier transforms of the signals respectively being fed into channels A and B of the analyser 19. The phase angle difference $\phi_{XFRn}$ is given by the expression $$\phi_{XFRn} = \phi_{Bn} - \phi_{An}$$

Since $\phi_{An}$ and $\phi_{Bn}$ contain identical errors the subtraction eliminates the error in $\phi_{XFRn}$.

The phase angle difference $\phi_{XFRn}$ of each component is the difference in phase between corresponding components of the fourier transform of the reference (or first) signal being fed to channel A of the analyser 19 and the fourier transform of the vibration (or second) signal being fed to channel B of the analyser 19. The phase angle of each component of the fourier transformed vibration signal relative to the keyway (the known shaft position) is known as the reconstruction phase angle $\phi_{Rn}$ and is given by the expression $$\phi_{Rn} = \phi_{XFRn} - \phi_{An}$$

where $\phi_{An}$ is the phase angle of the components of the fourier transformed reference signal as discussed above which contain errors. Thus if $\phi_{An}$ is known analytically for the number of harmonics of interest then an accurate value of the reconstruction phase angle $\phi_{Rn}$ can be obtained.

As described above the reference signal used in the preferred method comprises a series of impulses and has a mark to space ratio of less than 1/n where n is the number of selected vibration components for analysis. It can be shown that if the mark to space ratio is less than 1/n then the phase angles $\phi_{An}$ of the first n components of the fourier transformed signal are equal to zero. The reconstruction phase angle $\phi_{Rn}$ is therefore equal to the phase angle difference $\phi_{XFRn}$ for all selected harmonics.

The reconstruction magnitude values $B_n$ and phase difference $\phi_{XFRn}$ corresponding to the reconstruction phase angles $\phi_{Rn}$ are transmitted from analyser 19 via interface 23 and stored in the computer 24.

The above described process can be repeated using a vibration (or second) signal firstly from proximity probe 14 and then from proximity probe 16 to obtain reconstruction magnitude values and corresponding reconstruction phase angles for vibration in each of three directions. From these values vibration of the shaft in time along a three cartesian axes can be plotted, for example, by means of plotter 26. The measurement axes of the probes 14, 15 and 16 need not be mutually perpendicular since the reconstruction magnitude values and corresponding reconstruction phase angles form vector qantities so that transformation to any co-ordinate system can be effected by vector algebra.

Measurements similar to those above can be made at a number of points, along a shaft for example at each bearing to obtain vibration information for the length of the shaft.

The above described measurements can also be conducted at "slow roll" shaft speeds to obtain reconstruction magnitude values and corresponding reconstruction phase angles which can be subtracted using vector algebra from the operating speed measurements to provide a detector calibration correction.

The displacement of the bearing casing 13 (FIG. 1) in each direction can also be measured with respect to ground using the above described method and accelerometers 26, 27 and 28. The accelerometers 26, 27, 28 are selected one at a time via switch 29 to provide a displacement signal to channel B of the analyser 19. These measurements can be adjusted to the same co-ordinate system as the shaft measurements and vectorially added to obtain absolute shaft displacement. In some applications, computer compensation is necessary to allow for low frequency cut off phase errors introduced by double integration of the accelerometer signal.

Figure 2:
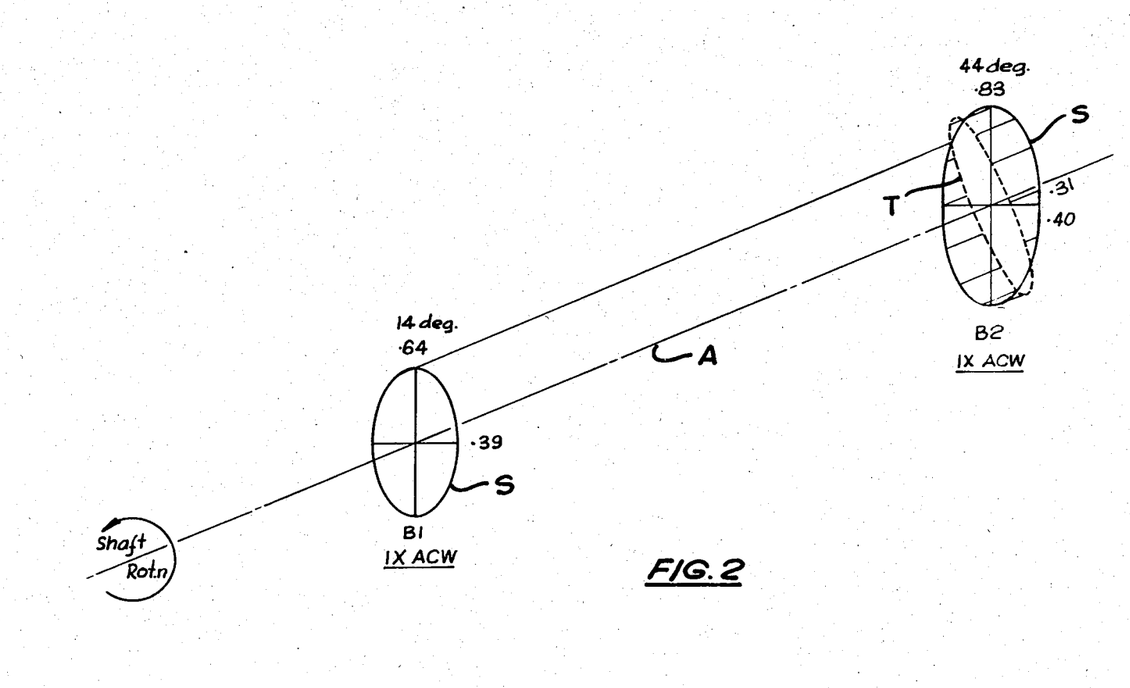
FIGS. 2 to 5 are exemplary plots of three dimensional waveform reconstruction data obtained according to the preferred method.

Once the various reconstruction magnitude values and reconstruction phase angles have been stored in computer 24 any desired combination can be plotted by means of plotter 25. For example, FIG. 2 is an exemplary plot of three dimensional "slow roll" shaft displacement only at each of two bearings B1 and B2 supporting the rotating shaft.

The broken line A is the nominal axis of the shaft and the curves S represents the path apparently followed by the axis of the rotating shaft due to mechanical and permeability errors. The curve T is the 3 dimensional motion of the shaft using axial data. The values 14 deg and 44 deg adjacent the curves S represents the "high spot" on the shaft at each bearing relative to the vertical axis at the instant the keyway 21 is under the phase reference probe 20.

The vertical and horizontal peak to peak relative displacements in mils (0.001 inch) are indicated by the values 0.64 and 0.39 appearing above and to the side of curve S corresponding to bearing B1. Similarly, the values 0.83 and 0.41 adjacent curve S at bearing B2 indicate the vertical and horizontal peak to peak relative displacements at bearing B2 while the value 0.31 typed in alignment with axis A adjacent curve S for bearing B2 indicates the peak to peak axial relative displacement. The same nomenclature has been used in FIGS. 3 to 5.

Figure 3:
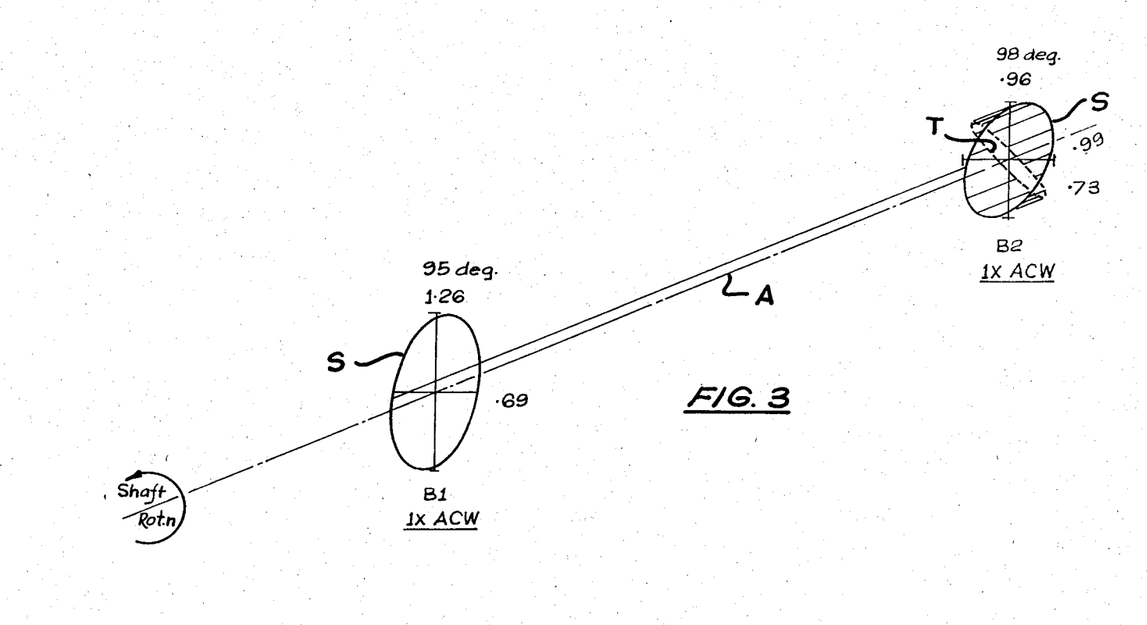

FIG. 3 is an exemplary plot of three dimensional true relative (to bearing casing) shaft displacement at the same two bearings B1 and B2, that is full speed relative displacement minus "slow roll" displacement.

Figure 4:
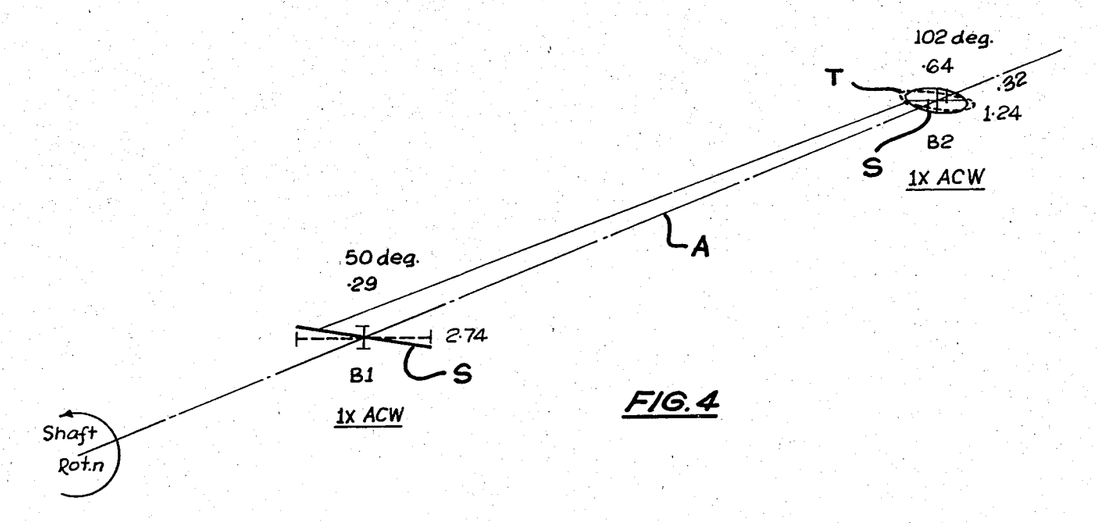

FIG. 4 is an exemplary plot of three dimensional casing displacement adjacent each of the bearings B1 and B2.

Figure 5:
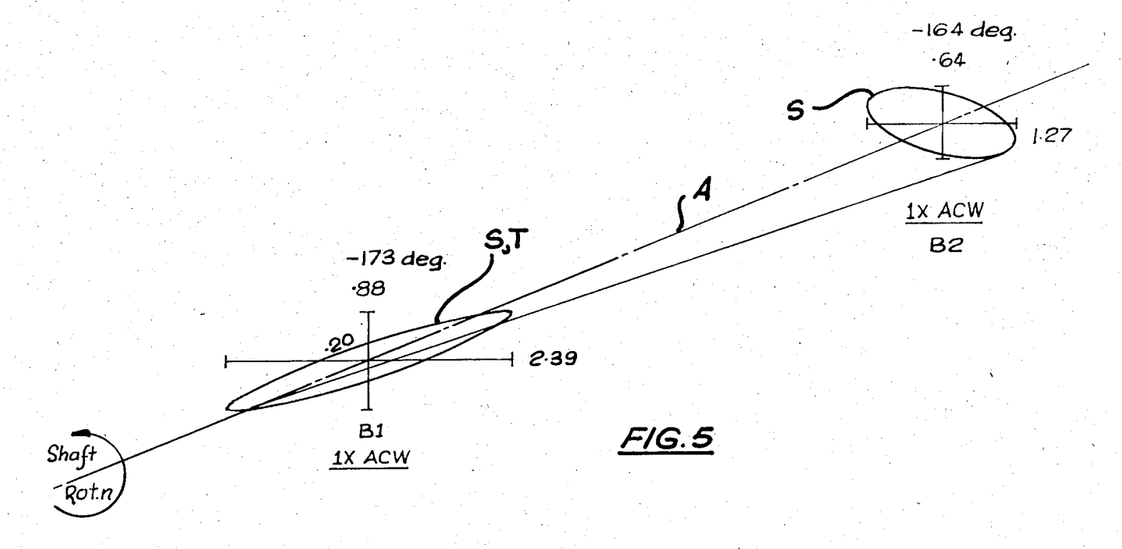

FIG. 5 is an exemplary plot of three dimensional absolute shaft displacement at each of bearings B1 and B2. That is, relative shaft displacement minus "slow roll" displacement plus casing displacement.

The plots of FIGS. 2 to 5 show only the displacement occurring at the frequency of shaft rotation for the sake of clarity. It will be apparent however, that the data can be presented in many forms, for example each harmonic separately, selected harmonics summed or overlaid, or any other required combination.

The present invention enables performance of advanced dynamic analysis of machinery using the standard single function transducers, digital processing and post processing in the frequency domain and data presentation in both frequency and time domains. As will be apparent to those skilled in the art from the teaching hereof, the latter is especially advantageous. This new approach of analysing and post processing in the frequency domain exclusively allows all previously possible analysis to be conducted more efficiently and allows a number of new types of analysis. The following describes some of the applications of the above described measurement techniques.

The above described method can also be used in conjunction with measurements of parameters such as Mobility of the casings supporting bearings to calculate bearing forces and hence balance correcting weights as will be described below. The vibration response of the machine casing can be measured using substantially the method described above by connecting channel A of a FFT analyser to a load cell which measures an input force. Input force can be generated by for example, an impacter or shaker and applied preferably in three different directions adjacent each bearing. The directions are chosen to allow resolution of the input forces into a three dimensional cartesian co-ordinate system. Channel B of the FFT analyser measures the vibration response of the machine casing to the input force in a first direction and the vibration can be represented as a series of vectors in the manner described above. This process is repeated for each of three directions so that the vibration response of the casing can be determined with reference to the co-ordinate system. In a shaft supported by two bearings, for example, the force applied at one of the bearings and measured in a given direction at the second bearing should be the same as if the force were applied at the second bearing and measured in the same given direction at the first bearing. Thus, up to forty percent of the number of measurements normally required need not be made since the corresponding force effects can be assumed to be the same.

The above described data can be used to calculate the force exerted at various bearings supporting a rotating shaft. The force F in newtons is calculated according to the equation $$F = \frac{\text{machine case operational forced mode shape in mm}/S}{\text{machine case Mobility parameters in mm}/S/N}$$

for frequencies corresponding to shaft speed and harmonically related frequencies.

The force vectors in three dimensions can therefore be obtained by measuring the following:
(a) case vibration at each bearing in three planes at the required machine speed; and
(b) case mobile parameters across a frequency range to include shaft speed and several harmonics thereof.

From this data it is possible to determine the forces acting at each bearing in each of three orthogonal directions relative to the shaft phase reference (the keyway in the above described method) for each harmonically related vibration. This calculation is performed by computer using substantially conventional matrix manipulation.

Once the force distribution on the machine at each bearing is obtained an estimation of the percentage of imbalance and percentage of misalignment can be made. This estimation is aided by refernce to the components of the shaft displacement waveform since high first harmonic vibration is usally indicative of imbalance whereas shaft misalignment usually involves contributions by second and higher components and 180° phase changes across flexible couplings. From the estimation of percentage imbalance and percentage misalignment standard mechanical engineering moment and force calculations can be used to determine the weight changes necessary to negate the force imbalance.

In the case of flexible shaft machines a substantially conventional mathematical shaft model can be used in conjunction with Nyquist and modal data to estimate the weight changes at the various balancing planes. These calculations determine the weight changes required to prevent the shaft "bowing" excessively as it nears resonant frequencies, not the weight changes required to negate the resonant "bowed" shape once it has established itself. It will be apparent that the above described method of vibration analysis not only provides for new forms of analysis but also allows the data used to be conveniently stored in a digital computer, for example. This is particularly important in the case of "slow roll" data which can often only be obtained on very infrequent occasions.

We claim:
1. A method for measuring vibration in a machine including a member under periodic motion, said method comprising the steps of:

(a) selecting specific vibration harmonic components to be measured;

(b) generating by first sensor means a first signal that repeats every period of said motion to provide a reference to a known position on the member, a frequency domain transform of said first signal having known harmonic component phase angles relative to said known position for all said selected harmonic components;

(c) generating by second sensor means a second signal which varies in the time domain with respect to a vibration characteristic of the machine;

(d) transforming the second signal into a frequency domain to derive a plurality of third (reconstruction magnitude) signals each indicative of the magnitude of one of the selected harmonic components of the transformed second signal, and synchronously transforming the first signal into the frequency domain to derive a fourth signal for each selected harmonic, each fourth signal being indicative of the phase angle difference between corresponding harmonic components of the transformed second signal and the transformed first signal; and (e) storing said third signals and said fourth signals.

2. A method as claimed in claim 1 wherein the transform of the first signal and the second signal into the freqency domain comprises a fourier transform.

3. A method as claimed in claim 1 further comprising the steps of obtaining for each selected harmonic component a fifth (reconstruction phase angle) signal indicative of the difference between each said fourth signal and a corresponding one of a plurality of sixth signals, each one of said sixth signals being indicative of one of the known harmonic component phase angles of said first signal; and storing said fifth signal.

4. A method as claimed in claim 1 wherein said member under periodic motion comprises a rotating shaft and wherein the reference signal repeats every shaft revolution.

5. A method as claimed in claim 4 wherein the first signal comprises a series of impulses, one impulse occuring each shaft revolution.

6. A method as claimed in claim 5 wherein the mark to space ratio of the first signal is less than $1/n$, where n is the total number of selected harmonics, whereby the known harmonic component phase angles of the first signal for each selected component are zero.

7. A method as claimed in claim 5 wherein said first sensor means comprises a detector located adjacent the shaft which causes an impulse each time it detects the passing of marking on the shaft.

8. A method as claimed in claim 1 wherein the simultaneous transforms of the first and second signals is effected by fast fourier transforms.

9. A method as claimed in claim 8 wherein the fast fourier transforms are performed by a multi-channel fast fourier transform analyser.

10. A method as claimed in claim 1 wherein the fourier transformed first and second signals are frequency averaged.

11. A method as claimed in claim 1 wherein the selected harmonic components include at least the first twelve integer harmonic components.

12. A method as claimed in claim 1 wherein said vibration characteristic is displacement of the member relative to a reference position.

13. A method as claimed in claim 12 wherein the second signal varies in the time domain with respect to displacement of the member in a first direction and the method further comprises repeating each of steps (a) to (e) for each of two further second signals which respectively vary in the time domain with respect to displacement of the member in second and third directions, the first, second and third directions being non-parallel.

14. A method as claimed in claim 13 wherein the first, second and third directions are mutually perpendicular.

15. A method as claimed in claim 1 wherein said machine includes a casing supporting said member and wherein said vibration characteristic is displacement of the casing relative to a reference position.

16. A method as claimed in claim 15 wherein the second sensor means comprises an accelerometer and displacement is measured by twice integrating the output of the accelerometer with respect to time.

* * * * *